United States Patent
Wilson et al.

(10) Patent No.: US 8,803,700 B1
(45) Date of Patent: Aug. 12, 2014

(54) EVENT NOTIFICATION SYSTEM FOR ALERTING THE CLOSEST APPROPRIATE PERSON

(71) Applicant: Globestar Systems, Inc., Toronto (CA)

(72) Inventors: Jason Wilson, Toronto (CA); Raul Sinimae, Toronto (CA)

(73) Assignee: Globestar, Inc., Toronto (CA)

( * ) Notice: Subject to any disclaimer, the term of this patent is extended or adjusted under 35 U.S.C. 154(b) by 9 days.

(21) Appl. No.: 13/757,117

(22) Filed: Feb. 1, 2013

(51) Int. Cl.
*G08B 21/00* (2006.01)
*G08B 21/18* (2006.01)

(52) U.S. Cl.
CPC .................................. *G08B 21/18* (2013.01)
USPC ................ 340/686.6; 340/573.1; 340/539.23; 340/286.07; 340/572.1

(58) Field of Classification Search
CPC ............. G08B 21/182; G08B 21/0247; G08B 21/0288; G08B 21/028; G08B 21/0269; G08B 13/14; G08B 21/22; G08B 21/24; G08B 21/0275; G07C 1/10; G07C 9/00111
USPC .......... 340/686.6, 686.1, 573.1, 573.3, 573.4, 340/539.13, 539.1, 539.21, 539.23, 286.07, 340/572.1
See application file for complete search history.

(56) References Cited

U.S. PATENT DOCUMENTS

| | | | |
|---|---|---|---|
| 7,012,534 B2* | 3/2006 | Chaco | 340/573.1 |
| 8,457,656 B2* | 6/2013 | Perkins et al. | 455/456.1 |
| 8,466,777 B2* | 6/2013 | Matsumoto et al. | 340/10.5 |
| 8,508,363 B2* | 8/2013 | Raniere | 340/539.32 |
| 2003/0144011 A1* | 7/2003 | Richards et al. | 455/456 |
| 2010/0309002 A1* | 12/2010 | Duvall et al. | 340/573.4 |

* cited by examiner

*Primary Examiner* — Anh V La
(74) *Attorney, Agent, or Firm* — Robert Schuler

(57) ABSTRACT

A healthcare system includes an event notification system, a real-time location system and a proximity notification function. The event notification system operates to receive event messages from an event generation device, the real-time location system operates to receive tag identity and location information from a tag detector and the proximity notification system operates to receive the tag identity and location information and determine which of a plurality of tags are closest to the source of an event and to send an event alert message to an individual associated with this tag.

22 Claims, 6 Drawing Sheets

HEALTHCARE SYSTEM 100 (PRIOR ART)

HEALTHCARE SYSTEM 200 (PRIOR ART)

FIG. 4

MAP 332

| PHYSICAL LOCATION OBJECT | LOGICAL LOCATION OBJECT | | |
|---|---|---|---|
| | OFFSET | ABSOLUTE | OBJ. ID |
| HOSPITAL 401 | (0, 0, 0) | (0, 0, 0) | HOSP. |
| MAIN BLDG | (10, 10, 10) | (10, 10, 10) | MB |
| WING A | (10, 10, 10) | (20, 20, 20) | WA |
| WING B | (-5, 10, 10) | (5, 20, 20) | WB |
| FIRST FLOOR | (-5, 10, 5) | (0, 30, 15) | FL.1 |
| SECOND FLOOR | (-5, 10, 15) | (0, 30, 25) | FL.2 |
| HALLWAY | (-4, 11, 0) | (-4, 41, 25) | H.W. |
| ROOM 201 | (-3, 12, 0) | (-7, 53, 25) | R.201 |
| ROOM 202 | (-3, 13, 0) | (-7, 54, 25) | R.202 |
| NURSE CALL | (-3, 14, 0) | (-7, 55, 25) | N.C. |
| BREAKROOM | (1000, 1000, 1500) | (996, 959, 1475) | B.R. |

EVENT NOTIFICATION SYSTEM FOR ALERTING THE CLOSEST APPROPRIATE PERSON

FIELD OF THE INVENTION

The present disclosure relates to an event notification system that is able to identify and send an alert to an appropriate individual that is also closest to an event.

BACKGROUND

In certain settings, it is necessary to be able to initiate a request for assistance that is automatically distributed to an appropriate individual. Systems are in use that receive event messages from one or more event generation devices, process the event message to identify which of one or more individuals should receive a message alerting them to the event occurrence, and to transmit an alert message to the identified individual(s). These systems are typically referred to as Event Notification Systems (ENS) and they can be useful in healthcare settings, emergency management settings, retail or commercial settings, and in many other settings. For the purposes of this description, an ENS will be described in the context of a healthcare setting.

FIG. 1 is a diagram of a healthcare network 100 that includes an Event Generation Device (EGD) 110, an Event Notification System 120 (ENS), and an Alert Message Recipient (AMR) 130. The EGD 110 can be in communication via a wired or wireless network link with the ENS 120, and the ENS 120 can be in communication with the AMR 130 over a wired or wireless link. In a hospital setting the AMR can be any member of a hospital staff, such as a doctor or a nurse. In a hospital setting, the EGD 110 can be, among other things, a piece of equipment such as a heart or respiration monitor, it can be a communication device located in an emergency room or intensive care unit operated by staff for the purpose of requesting supplies or other staff, or it can be a nurse station. Each EGD 110 can transmit event messages that comprise the identity of the originating device, the time the message is transmitted and information particular to the purpose of the alert message, such as a request for supplies, a request for a staff member, or an indication that a particular patient's heart has stopped all of which collectively can be referred to as an event identity. The ENS 120 generally operates to, among other things, receive event messages, examine their contents and determine to which recipient or recipients an alert message comprising information in the event message should be forwarded. In a healthcare and other settings, it is often important to identify and alert the staff member or members closest to the origin of an event of the event occurrence. FIG. 2 is a diagram of a healthcare system 200 having functionality that operates to identify and to track the locations of mobile objects for the purpose of identifying and notifying the closest staff member to an event of the events occurrence.

The healthcare system 200 of FIG. 2 can in implemented in one or more servers (not shown) which are connected to a network (local or wide-area network) and be configured to include all of the same functionality as the healthcare system 100 described earlier with reference to FIG. 1, with the exception that it also comprises a real-time location (RTL) system 210 having a plurality of wireless RTLS tags 230 and a plurality of tag detection devices 220 that operate to receive information relating to any one of the plurality of the RTL system tags 230. The tag detectors 220 can transmit information received from a tag over a network link to the RTL system 210. The tag location detection device 220, or simply detector 220, can be strategically positioned to detect the presence of a tag 230 within range of the detector in some or all of a plurality of specified facility locations. These locations can correspond to particular buildings, floors, hallways, rooms or other specified locations in a particular facility. The RTL system 210 is also comprised of a listing of tag identities 215 and a listing of tag detector locations 225, wherein the tag identity 215 can be any unique coded information specified by a system administrator and each tag detector location 225 can correspond to an actual, physical location such as a building, a floor, a hallway, a room, etc. and both the tag identities 215 and the tag detector locations 225 can be stored in non-volatile memory comprising the healthcare system 200. The RTL system 210 can be designed to operate with either active or passive location tags. In the case where the system is operating with passive tags, the system includes a transceiver that periodically sends out a signal that activates circuitry in the passive tag causing it to transmit tag information (typically a tag ID) back to the system 210. In the case of active tags, each tag includes a battery to power transmitter circuitry that operates to periodically transmit a signal that includes, among other things, the identity of that tag. In operation, a tag worn by a staff member or attached to a piece of mobile medical equipment comes into range of a tag detector 220 which detects the presence and identity of the tag and transmits the tag ID and detector location ID to the RTL system 210, which then stores the then current tag location in non-volatile memory associated with the healthcare system 200 for later use.

In addition to the RTL system 210 described with reference to FIG. 2, the system 200 also comprises an event notification system (ENS) 240 similar to the system 120 described earlier with reference to FIG. 1. In addition to the functionality comprising the ENS 120, ENS 240 has proximity notification functionality 250 that operates to detect one or more appropriate staff members closest to the source of an event, to notify the one or more identified staff members of the event and then direct them to the source of the event.

BRIEF DESCRIPTION OF THE DRAWINGS

The present invention can be best understood by reading the specification with reference to the following figures, in which:

FIG. 4 is a diagram showing a physical location object to logical location object map 332.

DETAILED DESCRIPTION

Figure 1:
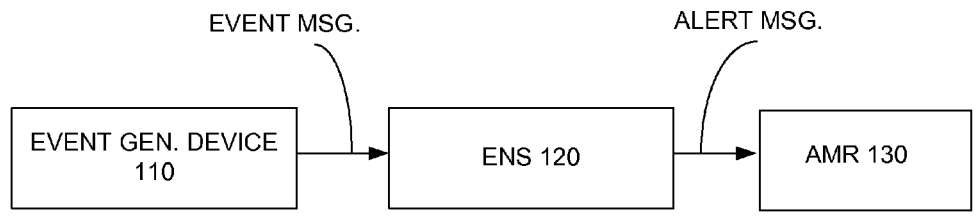
FIG. 1 is a diagram of a healthcare system 100.

In some cases the staff member who is closest to the source of an event is not the most appropriate individual to be notified of the event. For instance, if a staff member who is identified as being closest to the source of an event is on break, then this individual may not be the most appropriate person or should not be notified of the event's occurrence. Further, in the case that a tag detector located on one floor detects a tag located on a different floor, an appropriate staff member located on the different (lower or higher) floor than the floor on which the event is generated may actually be closer to the source of an event than a staff member on the same floor as the source of the event, but take much longer to respond to the event than the staff member on the same floor as the event. Or, in the case that the closest staff member to an event has previously responded to and is currently servicing a higher priority event, then this staff member may not be the appropriate person to send an alert to.

One way to resolve this problem is to track the activities and/or schedules of each staff member so that it is known they are on break, or they are involved with a higher priority event, in which case an RTL system may or may not notify that staff member of an event. Another way to resolve this problem is to use line-of-sight location technology such as infrared technology for example. However, sometimes staff members neglect to notify the RTL system that they are on break, or they fail to notify the system that they are currently attending to an event, or because of the application it is not desirable to employ infrared or other technology. In lieu of the limitations of the prior art proximity based event notification methods, it was discovered that a plurality of logical location objects, each one relating/corresponding to at least one of a different physical location object, can be created and assigned logical location coordinates that places each logical location object into a three dimensional logical space relative to each other logical location object. A logical location object corresponding to a physical location object may or may not be assigned coordinates that are substantially the same as coordinates assigned to the corresponding physical location object. The logical location coordinates can correspond to a physical, linear distance or correspond to a logical distance which has no relationship to a physical, linear distance. In one embodiment, a logical location object is assigned coordinates according to the type of a physical location object that it corresponds to. In another embodiment, a logical distance threshold is employed to determine whether to send an alarm message or not. In another embodiment, a staff member whose current position is detected to be within the boundary of a logical location object, and this location object is logically distant from an event by greater than a logical distance threshold value, is not notified of an event unless the event is escalated to a selected level or escalated some number of times.

Figure 3A:
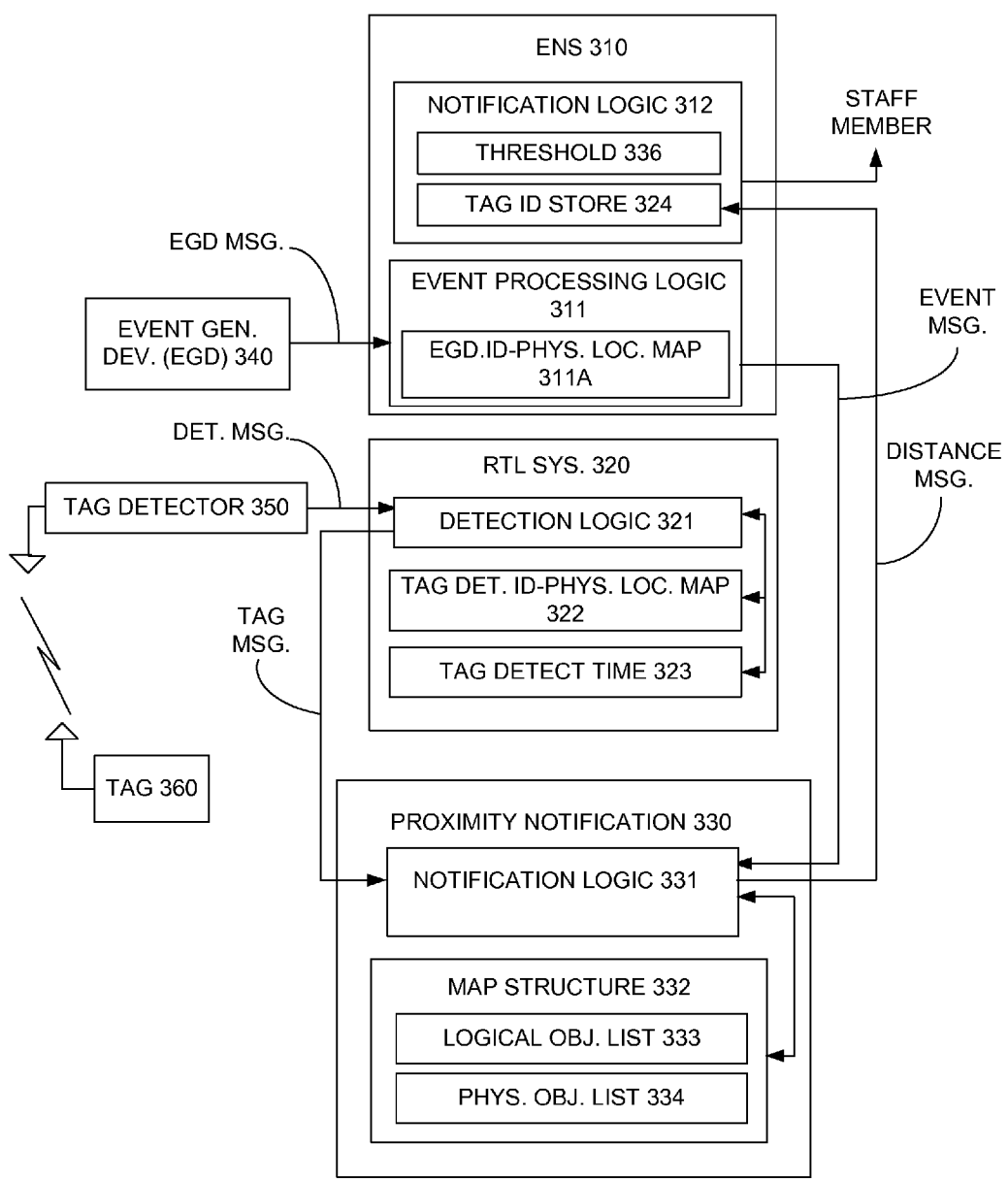
FIG. 3A is a diagram illustrating one embodiment of a healthcare system 300

FIG. 3A is a diagram of an Event Detection and Notification network 300, such as a healthcare system, showing functional elements comprising the network. This network has an event notification system (ENS) 310, an RTL system 320, and a proximity notification (PN) function or system 330. Each of the ENS 310, RTL 320 and PN 330 can be implemented in computer program code stored in a non-volatile memory device associated with the same or different computational devices. The computational device(s) can be a network server or any other device that is suitable for running the computer program code and for communicating over a network with other devices and functionality comprising the network. The ENS 310 is connected over a network to one or more event generation devices (EGD) 340, such as a nurse call station or hospital bed patient monitoring equipment, an emergency room or operating room communication device, or any other device that operates to generate an EGD message that that can include the identity of the EGD (EGD.ID) and the type of event. The EGD message can be transmitted to the ENS 310 where event processing logic 311 comprising the ENS 310 can examine the EGD message for the EGD.ID, map the EGD.ID to a physical location within the hospital using a EGD.ID to physical location map 311A, and send an event message to the proximity notification function 330 that includes the physical location of the source of the event and the event source (nurse call, hospital bed, etc.).

Continuing to refer to FIG. 3A, the RTL system 320 can be connected over a network to one or more tag detectors 350, each of which operates to detect the presence of one or more tags 360. Each tag 360 can be worn by a staff member or it can be attached to a piece of mobile medical equipment. Generally, a tag is considered to be attached to an object, whether the object is a staff member or whether the object is an item of mobile equipment. When a tag 360 comes into range of a tag detector 350, the tag detector operates to request unique tag ID information stored on the tag, and to send a message to the RTL system 320 that comprises the unique tag ID information, the identity of the tag detector and the time that the tag is detected. The RTL system 320 can include detection logic 321, a tag.id to physical location map 322, and a tag detection time store 323. The detection logic 321 operates to receive the detector message (DET.MSG.) and to examine the message for a unique tag detector ID, information corresponding to an identity of the tag (tag.id), and possibly the detection time, and uses the map 322 to associate the tag detector ID with a physical location within the hospital in order to determine the current physical location of the tag. The physical location identified as being the current location of the tag and the unique tag ID can be sent to the proximity notification function 330 in a Tag Message.

Continuing to refer to FIG. 3A, the proximity notification (PN) function 330 comprises notification logic 331 and a map structure 332 that serves to relate each of a plurality of physical location objects comprising a listing 334 to a particular one of a plurality of logical location objects comprising a listing 333. Each of the physical location objects comprising the listing 334 is associated with a particular physical location within the hospital facility that is identifiable on a facility floor plan, such as the floor plan(s) represented in FIG. 5. The listings 333 and 334 are organized in a logical hierarchy of nested location objects, and each logical location object comprising the list 333 is assigned a set of logical location coordinates that positions each logical location object within a logical three dimensional space relative to and offset from an immediate parent node with respect to that object. The structure of the lists 333 and 334 and the methodology employed to assign the logical location coordinates is described later with reference to FIG. 4. Generally, the notification logic 331 operates to receive an event message, and uses information in this message to calculate a logical distance between a logical location of the event source and a logical location of each tag that is detected by the RTL system 320.

Figure 3B:
FIG. 3B is a diagram showing the functional elements comprising a proximity notification function 330.

More specifically as shown in FIG. 3B, a tag location processing function comprising the notification logic 331 receives tag messages from the RTL system 320 that includes information relating to the current physical location of a detected tag and the tag identity (Tag ID), and stores this information in a tag location store. An event location processing function comprising the notification logic 331 receives an event message from the ENS 310 that includes information relating to the physical location of an event source and the identity of the event source and stores this information in an event location store. The tag location and the event location processing functions use the physical location information in the tag message and the event message to identify physical location objects in the listing 334 corresponding to the tag location and to the event location, and then use the map structure 332 in FIG. 3A to associate each identified physical location object comprising list 334 with a logical location object comprising list 333. As will be described with reference to FIG. 4, each logical location object comprising list 333 is assigned a set of logical location coordinates, and these logical location coordinates are employed by a logical distance calculation function, comprising the notification logic 331 in FIG. 3B, to calculate a logical distance between the logical location of an event source and a current logical tag location in comprising the store 325. Subsequent to calculating a logical distance between two objects, the notification logic 331 can send a distance message to the notification logic that includes the identities of one or more tags and the logical distance between each tag and an event source for storage in a Tag ID store 324 comprising the notification logic 312. The notification logic 312 also includes a value 336, that can be configured by a system administrator, which represents a logical distance threshold from an event source to a tag. The store of tag identities (available tags) 324 can be examined by the notification logic 312 in the ENS 310 in order to determine which staff should receive an alert message in respond to an event.

The notification logic 312 comprising the ENS 310 has, among other things, functionality that is specifically designed to make decisions regarding which staff are to be notified as the result of the ENS 310 receiving particular event messages. This logic can be designed to notify staff according to their logical distance from an event source or disregard the logical or physical distance and notify staff that is physically proximate to an event source. The logic 312 can employ information in store 324 (logical distance) and a threshold value in the store 336 to determine whether an individual associated with the tag is within a logical threshold distance from an event source and should be notified of the event. Alternatively, this determination can be made according to an event priority (Hi, Medium, Low) for instance. In one embodiment, a notification message is sent to a staff member or object associated with a tag if the logical distance between the object and the tag meets a selected logical distance threshold rule. The threshold rule can be implemented in computer logic comprising the notification logic 312 running in association with the EMS 310, and the rule can control, among other things, the generation and sending of a message to a staff member notifying them of an event if a logical distance between the staff member and the event is less than or equal to a logical distance threshold value.

FIG. 4 illustrates the structure of map 332 which shows the correspondence between the physical location objects comprising the list 334 and logical location objects comprising the list 333. It can be seen in this map that the physical location objects are organized in a hierarchical, parent/child arrangement. In one embodiment, the locations are hierarchically organized in a campus, building, floor, wing, ward, room, bed arrangement, but the invention is not limited to this arrangement. Each parent node has one or more related child nodes and each child node has a related parent node (i.e., 2nd Floor is a parent node to Hallway), and each of the physical location nodes in the listing 334 correspond with or map to a logical location object comprising the listing 333. Each logical location object comprises a set of logical offset coordinates, a set of logical absolute coordinates and an object identity (ID). The logical location offset coordinates can be specified using an X, Y, Z Cartesian coordinate system, or any other three dimensional space coordinate methodology. According to one embodiment of the invention, a logical location object corresponding to a home or reference physical location object, such as a hospital complex, is assigned root node logical offset coordinates (0, 0, 0), and the hierarchy of objects is arranged such that logical location objects populating progressively lower levels in the hierarchy are assigned logical location coordinates that are offset from the coordinates assigned to a parent node immediately above it in the hierarchy of map 332. So, for instance, the logical location object labeled Wing A is a child node with respect to the logical location object labeled Main Building, and it is a parent node with respect to the object labeled 1st Floor, and the object labeled 1st Floor is a child node with respect to the object Wing A and is a parent object with respect to the logical location object labeled Hallway, and so forth. According to FIG. 4, the logical object labeled main building is assigned offset coordinates (10,10,10). The main building object is the parent object to an object labeled Wing B, and Wing B is assigned logical location coordinates (−5,10,10) that position it within a logical three dimensional space that is offset with respect to the Main Building object, which in this case is the parent to the object Wing B.

Continuing to refer to FIG. 4, each set of absolute logical location coordinates comprising a logical location object is calculated as the sum of all offset logical location coordinates that are assigned to immediate parent nodes going back to the root parent node, which in this case is the object labeled Hospital. Accordingly, the absolute logical location coordinates for Wing B are calculated by summing the offset coordinates assigned to the Hospital object, the Main Building object and the Wing B object, the result of which is (5,20,20). According to this logical location coordinate assignment methodology, the three logical location coordinates assigned to each logical location object correspond to logical distance values (or vector values) in each of three orthogonal directions (X,Y,Z) of the Cartesian coordinate system, but each of the three logical location coordinates can represent any unit value and need not represent a distance unit value.

Using this absolute coordinate value calculation method, the distance between any two logical location objects (i.e., the source of an event and an appropriate staff member) in a facility or within a three dimensional space can be easily calculated according to the following equation.

$$\text{Distance} = |\sqrt{[(X_1-X_0)^2+(Y_1-Y_0)^2+(Z_1-Z_2)^2]}| \qquad \text{Equation 1:}$$

According to Equation 1, the distance between any two logical location objects can be easily calculated by taking the absolute value of the square root of each of the squares of the differences between all three absolute coordinates associated with each logical location object. For example, if the source of an event is located in room 201 and an appropriate staff member to be notified of the event is located at the nurse call station, then using the absolute coordinates of the event source, or (−7, 55, 25) which correspond to $(X_1, Y_1, Z_1)$, and of the staff member's location, or (−7, 53, 25) which correspond to $(X_0, Y_0, Z_0)$, the distance is calculated to be approximately 2.0 distance units. While most of the absolute coordinate values of each of the logical location objects shown in FIG. 4 generally minors the physical location of physical location objects to which they map, this does not necessary have to be the case. According to an embodiment of the invention, the set of absolute coordinate values associated with any logical location object can correspond to a physical, linear distance or correspond to a logical distance which has no relationship to a physical, linear distance. This logical distance correspondence is illustrated in FIG. 4 in relation to the coordinates assigned to the break room (BR).

The offset logical location coordinates assigned to the logical location object identified as the Break Room (BR) are (1000, 1000, 1500), and these coordinates are assigned with the intent of logically distancing the Break Room from physical locations proximate to it, such as physical locations on the same floor, or the same wing, or the same building. According to an embodiment of the invention, the notification logic 312 comprising the ENS 310 can operate to notify only those staff members who are currently located or positioned in a facility within a specified, threshold logical distance from the location of a source of an event. If the value of the logical distance between the current location/position of a staff member and the location of an event source is determined by the notification logic 331 comprising the notification function 330 to be greater than the logical distance threshold, then, depending upon the configuration of the notification logic 312, the staff member may not be notified of the event at all, or may not be notified of the event until after it has escalated a specified number of times.

The term "appropriate" means herein that a staff member is available to respond to an event or not based upon whether or not they have appropriate medical training (doctor, nurse, other) to handle a medical event and whether the logical distance between a staff member and the event source places that staff member within a logical threshold distance from the event source or whether it places the staff member outside a logical distance threshold (in which case the staff member is not notified of the event or they are not notified of the event unless no other closer staff member responds).

Figure 2:
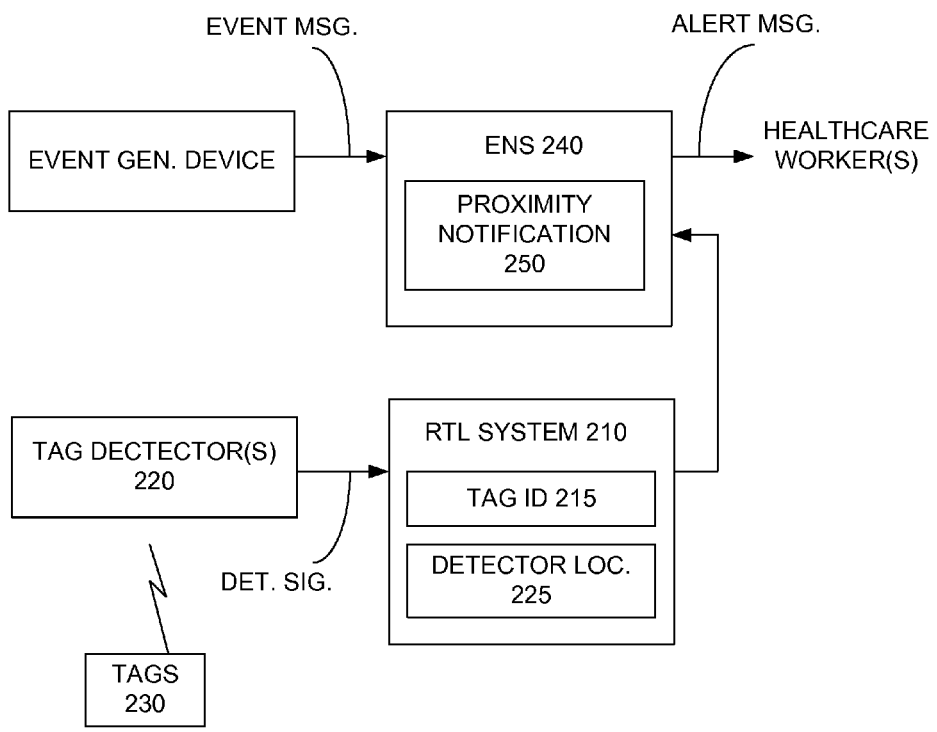
FIG. 2 is a diagram of a healthcare system 200 having location detection and proximity notification functionality.
Figure 5:
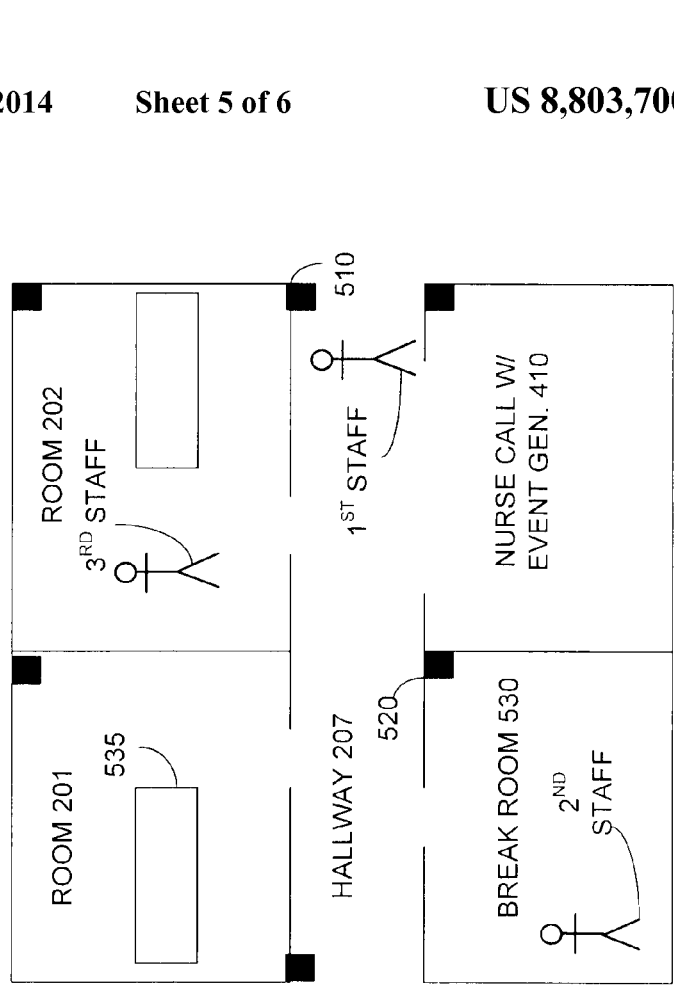
FIG. 5 is a facility floor plan of a main building.
Figure 5:
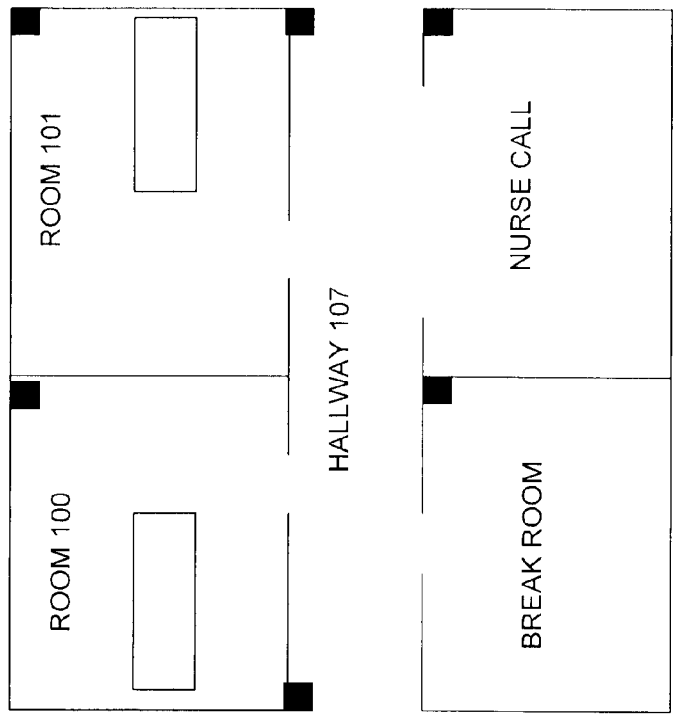
Figure 6:
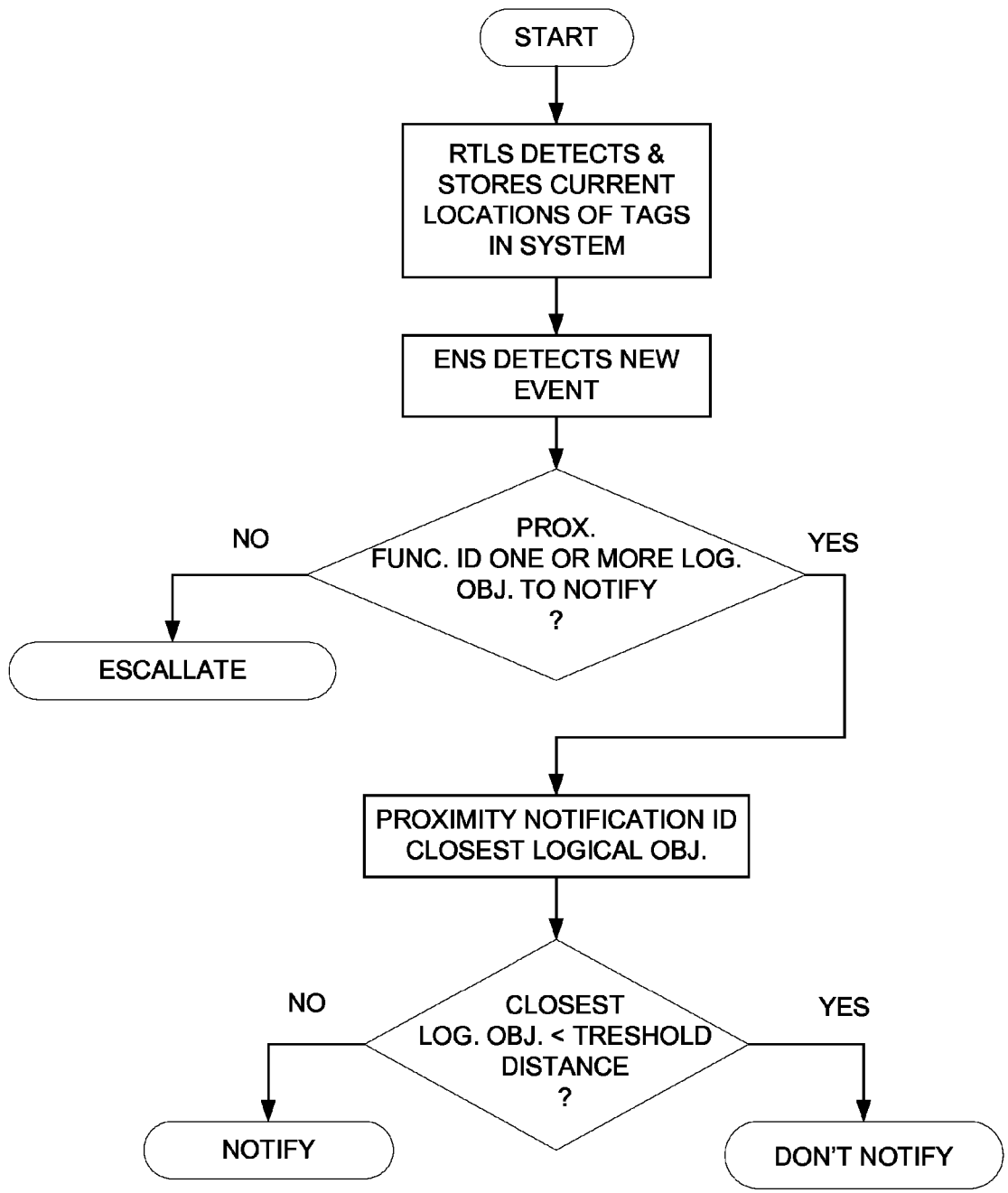
FIG. 6 is a logic flow diagram of an embodiment of the invention.

FIG. 5 illustrates a 1st and 2nd floor plan, located in a Wing B of a Main Building of the Hospital facility 401 described with reference to FIG. 4. The floor plan associated with the 2nd Floor is comprised of two patient rooms, RM201 and RM202, a Break Room, a Hallway, and a Nurse Call Station. Each of these areas represented in the floor plan corresponds to a physical location object in the listing 334 described with reference to FIG. 4, and each area has at least one tag detector 350 that operates to detect the presence of a tag 360 when a tag comes within range of the detector, and to send a message to a RTL system, such as the RTL system 210 described with reference to FIG. 2, comprising information that places the tag in the area at the time the tag is detected. As described earlier with reference to FIG. 4, each physical location object corresponds to at least one logical location object, and as previously described with reference to FIG. 3A, each logical location object can be assigned offset coordinates that place it at some specified/predetermined logical distance from a root node object and all other logical objects. Depending upon the notification strategy, the logical location coordinates assigned to each logical location object can substantially minor each corresponding physical location object's proximity to each other physical location object or not.

In one embodiment, the health care system 300 of FIG. 3 generally operates in the environment of the second floor, Wing B of FIG. 5 as follows. Assuming that a logical distance threshold 336 stored in the proximity notification function 330 is set to a logical distance of value "X", that a first staff member is detected to be within range of the tag detector 510 positioned at the far end of the Hallway 207 from Room 201, and that a second staff member is detected to be within range of the tag detector 520 position in the break room 530. Further, if an event generator associated with the hospital bed 535 in room 201 generates an event message, the message is transmitted over the hospital network to the RTL system 320 which detects the identity of the event generator in the message and is able to place the source of the event in room 201 (by comparing the event generator identity information in the event message to the store 322 to find a matching ID and mapping this ID to a facility map using the map 321). The location of the source event, which in this case is room 201, and the locations of the two staff members are sent to the proximity notification function 330 which correlates/maps the physical location objects (Hallway det. 510, break room 530, and room 201) to their corresponding logical location objects, and then calculates the logical distance between room 201 and the first staff member to be X+n (n being some integer value) and the distance between room 201 and the second staff member to be X−n, and then sends a message to the ENS 310 to send an alert message to the closest appropriate staff member to the event, which in this case is the first staff member. Despite the second staff member being physically closer (in the break room) to the source of the event (room 201) than the first staff member, the second staff member is not notified that an event message was generated in room 201, because the proximity notification module 330 determines that the logical distance between the second staff member and room 201 is greater than the value of the stored logical distance threshold 336 which in this case is "X". Alternatively, if the system 300 determines that more than one staff member is within the logical threshold X, it can be configured to notify the closest "N" staff members, with "N" being an integer value.

In other embodiments, the notification logic 312 can be designed such that the logical distance between any two or more objects is only one criteria employed in determining whether to notify a particular staff member of an event. Other criteria can include, but not be limited to, whether staff is busy tending to another event, the priority of the event, the occupational specialty associated with a staff member, to name only a few.

The forgoing description, for purposes of explanation, used specific nomenclature to provide a thorough understanding of the invention. However, it will be apparent to one skilled in the art that specific details are not required in order to practice the invention. Thus, the forgoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

We claim:

1. An event notification method, comprising:
    detecting, at one or more of a network device, information associated with a tag and an event generated by an event source;
    determining, using the information detected at the one or more of a network device, a current physical location associated with each one of the tag and the event source, and mapping the current physical location of the tag to a first logical location and the current physical location of the event source to a second logical location;
    calculating a logical distance between the first and the second logical locations; and
    generating and sending a message to an object associated with the tag notifying the object of the event provided that the calculated logical distance between the first and second logical locations meets a specified logical distance threshold rule.

2. The event notification and detection network of claim 1, wherein the object associated with the tag is an individual or an item of mobile equipment.

3. The event notification and detection network of claim 1, wherein the current physical location of each one of the tags and the event source is comprised of a set of physical coordinates.

4. The event notification and detection network of claim 3, wherein the set of physical coordinates defines a position of a physical location object within a three dimensional space.

5. The event notification and detection network of claim 4, wherein the physical location object is any one of a building, a building wing, a building floor, a hallway and a particular room.

6. The event notification and detection network of claim 4, wherein the physical location object corresponds to a logical location object.

7. The event notification and detection network of claim 1, wherein the first and second logical locations is comprised of a separate set of logical coordinates.

8. The event notification and detection network of claim 7, wherein the set of logical coordinates defines a position of a logical location object within the three dimensional space.

9. The event notification and detection network of claim 8, wherein the logical location object is any one of a building, a building wing, a building floor, a hallway and a particular room.

10. The event notification and detection network of claim 1, wherein the calculated logical distance comprises a linear distance measurement or a distance not related to a linear distance measurement.

11. The event notification and detection network of claim 1, wherein the specified logical distance threshold rule is comprised of a logical distance threshold value and one or more logical operators used to define the relationship between the calculated logical distance and the logical threshold value in order to determine whether or not to generate and send a message to the object.

12. An event detection and notification network, comprising:
a real-time location system connected to the network having one or more tag detectors for detecting a physical location and an identity of a tag associated with an object;
an event notification system connected to the network having one or more of an event source for detecting a physical location and an identity of an event;
a proximity notification system connected to the network for receiving the physical location of the tag and the event, the proximity notification system operating to separately map each of the physical locations of the tag and the event to a logical location and to calculate a logical distance between the tag and the event source, and the event notification system generating and sending a message over the network to an object associated with the tag notifying the object of the event provided the calculated logical distance between the event source and the tag meets a specified logical distance threshold rule.

13. The event notification and detection network of claim 12, wherein the object associated with the tag is an individual or an item of mobile equipment.

14. The event notification and detection network of claim 12, wherein the current physical location of each one of the tags and the event source is comprised of a set of physical coordinates.

15. The event notification and detection network of claim 14, wherein the set of physical coordinates defines a position of a physical location object within a three dimensional space.

16. The event notification and detection network of claim 15, wherein the physical location object is any one of a building, a building wing, a building floor, a hallway and a particular room.

17. The event notification and detection network of claim 15, wherein the physical location object corresponds to a logical location object.

18. The event notification and detection network of claim 12, wherein the logical location of each one of the tags and the event source is comprised of a set of logical coordinates.

19. The event notification and detection network of claim 18, wherein the set of logical coordinates defines a position of a logical location object within the three dimensional space.

20. The event notification and detection network of claim 19, wherein the logical location object is any one of a building, a building wing, a building floor, a hallway and a particular room.

21. The event notification and detection network of claim 12, wherein the calculated logical distance comprises a linear distance measurement or a distance not related to a linear distance measurement.

22. The event notification and detection network of claim 12, wherein the specified logical distance threshold rule is comprised of a logical distance threshold value and one or more logical operators used to define the relationship between the calculated logical distance and the logical threshold value in order to determine whether or not to generate and send a message to the object.

* * * * *